United States Patent [19]
Eggers

[11] Patent Number: 5,911,719
[45] Date of Patent: *Jun. 15, 1999

[54] RESISTIVELY HEATING CUTTING AND COAGULATING SURGICAL INSTRUMENT

[76] Inventor: Philip E. Eggers, 5366 Reserve Dr., Dublin, Ohio 43017

[ * ] Notice: This patent is subject to a terminal disclaimer.

[21] Appl. No.: 08/869,495

[22] Filed: Jun. 5, 1997

[51] Int. Cl.$^6$ .................................................. A61B 17/38
[52] U.S. Cl. ............................................. 606/31; 606/29
[58] Field of Search ........................... 606/27–31, 41–42, 606/45–50; 219/229–230, 233

[56] References Cited

U.S. PATENT DOCUMENTS

| | | | |
|---|---|---|---|
| 5,425,731 | 6/1995 | Daniel et al. | 606/28 |
| 5,480,397 | 1/1996 | Eggers et al. | 606/29 |
| 5,480,398 | 1/1996 | Eggers | 606/29 |
| 5,569,400 | 10/1996 | Lee | 219/233 |
| 5,611,798 | 3/1997 | Eggers | 606/31 |

*Primary Examiner*—John P. Leubecker
*Assistant Examiner*—Roy Gibson
*Attorney, Agent, or Firm*—Mueller and Smith, LPA

[57] ABSTRACT

A resistively heated thermally cutting and coagulating surgical instrument which may be employed with a conventional electrosurgical generator having bipolar output ports and a bipolar cable. The instrument utilizes a heating element which is heated to a predetermined upper temperature limit while in still air under a starting condition. Under this condition, heat dissipation by radiation, convection, and conduction through the instrument itself provides a high temperature end form of regulation. Under a subsequent working condition wherein the heated component or element is in contact with the tissue, heat dissipation is by thermal conduction both into the tissue and through the thermally conductive components of the instrument. A preferred heating element is formed with a ferromagnetic material which, when at the upper limit temperature is maintained at a value restricted to a temperature below curie temperature and which does not invoke surface oxidation or scaling within the time interval of heating experienced in the starting condition. However, the temperature is high enough to sustain a temperature effective for cutting and coagulation when in the working condition. A handle is employed which contains impedance matching circuit components. In one embodiment, the heating component of the instrument incorporates an integrally formed probe which is retained at lower temperatures through the use of a current restricting neck.

18 Claims, 8 Drawing Sheets

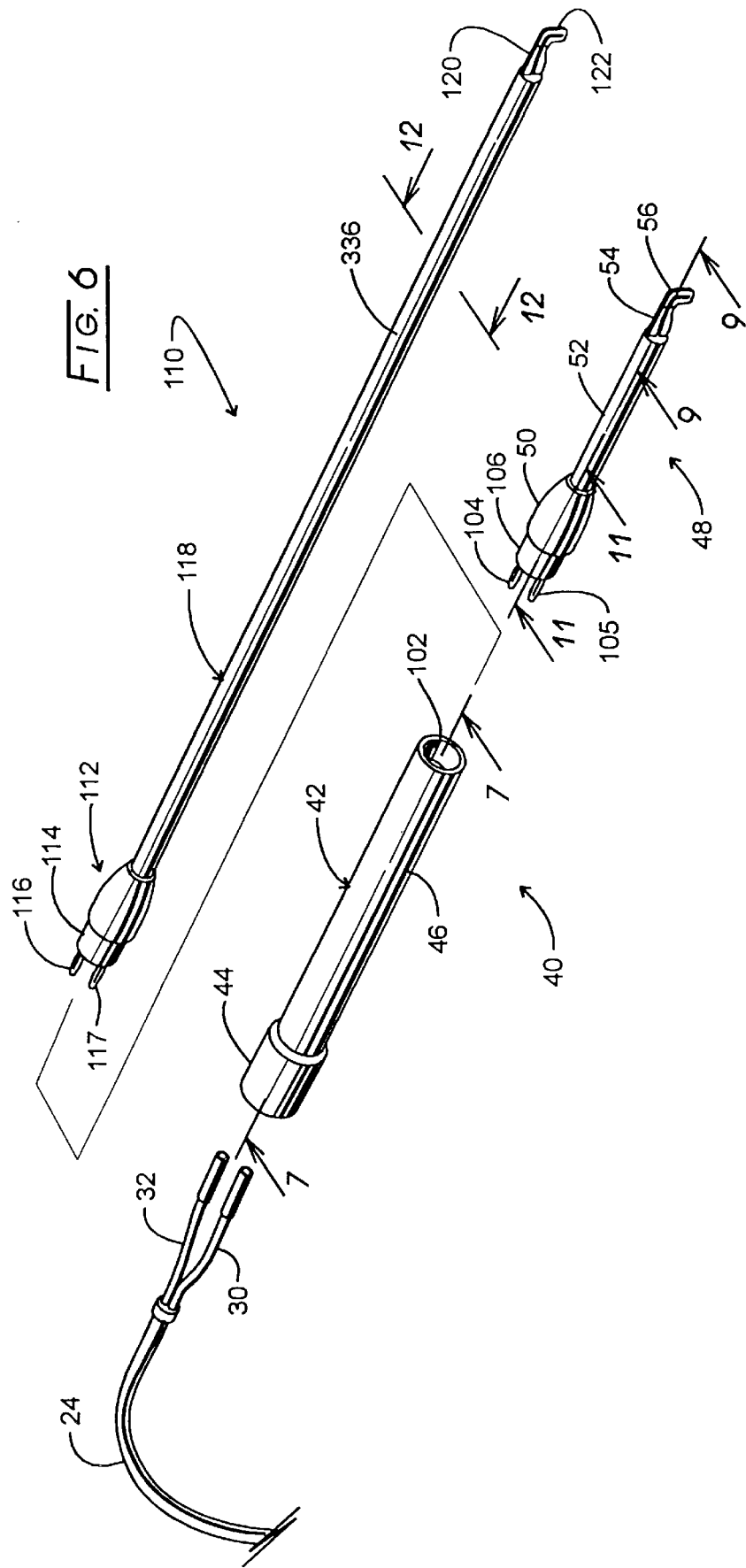

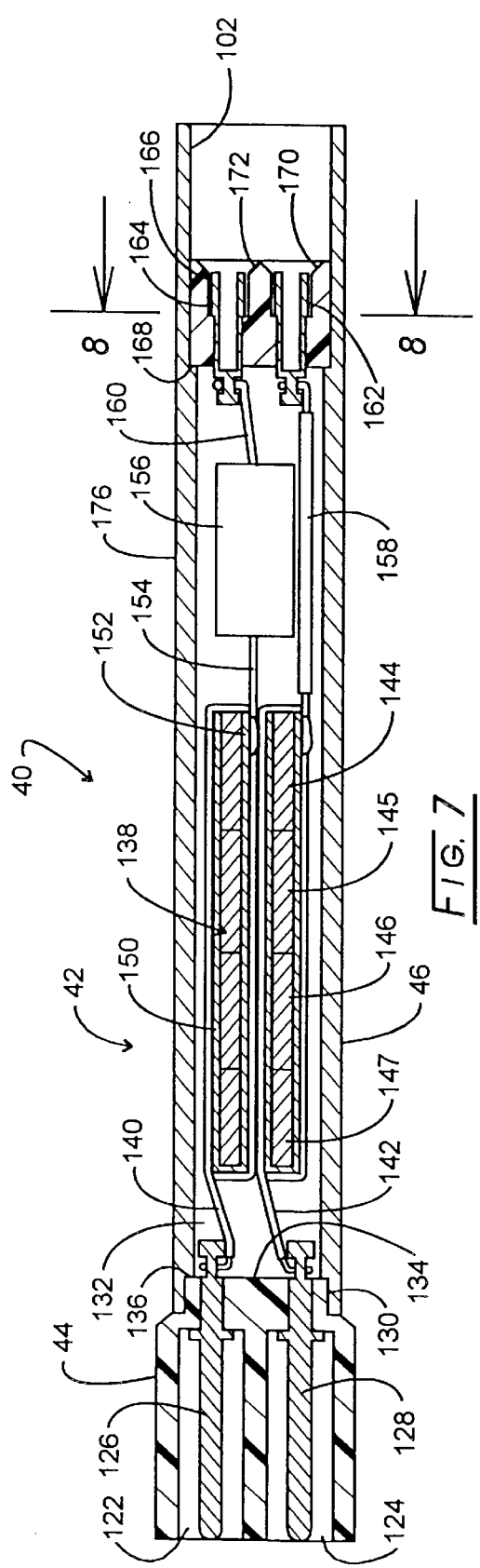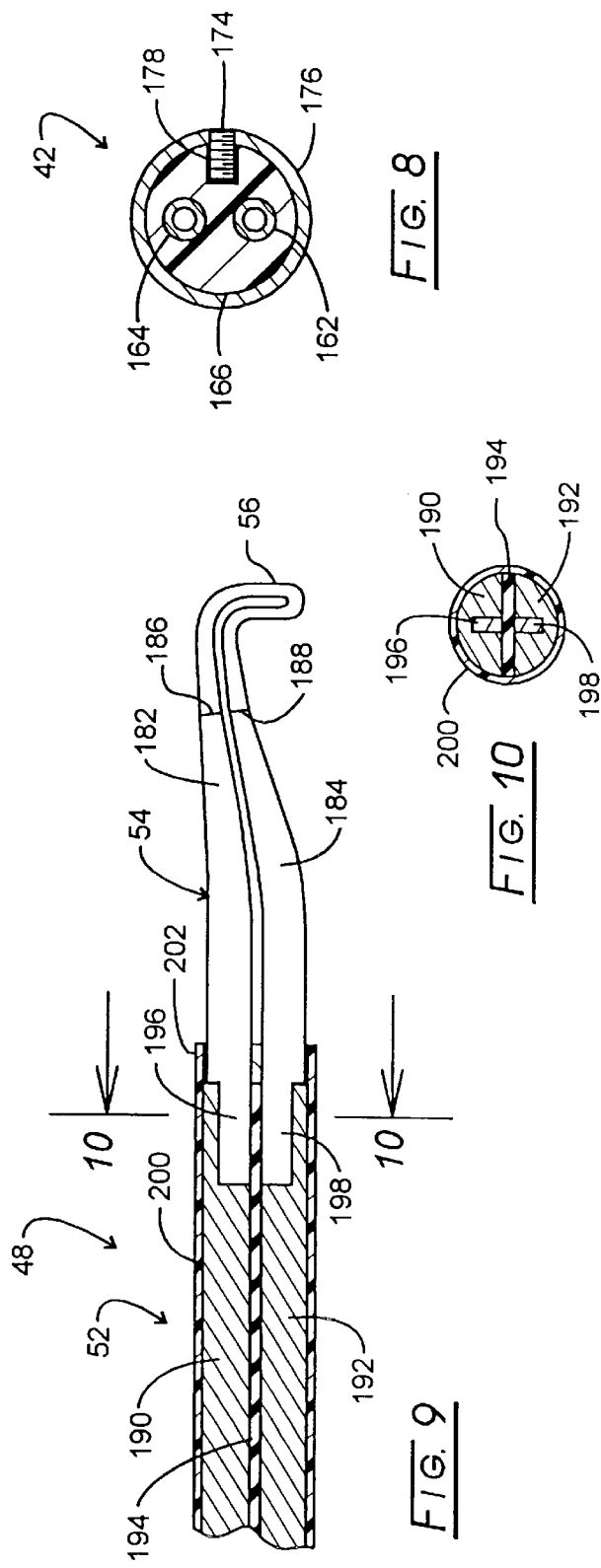

RESISTIVELY HEATING CUTTING AND COAGULATING SURGICAL INSTRUMENT

CROSS-REFERENCE TO RELATED APPLICATIONS

This application is related to U.S. Pat. No. 5,611,798 by Eggers, entitled: "Resistively Heated Cutting and Coagulating Surgical Instrument," issued Mar. 18, 1997.

BACKGROUND

Conventional surgical procedures are carried out utilizing a sequence of surgical instruments or tools. At the outset of a given procedure, sharp mechanical devices, such as the scalpel, are employed to part the skin layers so as to provide external access to the body cavity. Bleeding during such initial stages may be controlled through the use of ties, clamps, blotting procedures, and the like. As the body cavity is accessed, tissue not only is cut but is manipulated to the extent that mechanically sharp instruments often are supplanted by blunt counterparts. These blunt counterparts electrically perform cutting and blood coaggulating functions on demand through closure of a switch. Such electrosurgical technology has been available to surgeons for decades. For instance, a monopolar electrosurgical device was developed over sixty years ago by William T. Bovie. This early device described, for example, in U.S. Pat. No. 1,813,902, issued Jul. 14, 1931, entitled "Electrosurgical Apparatus" has met with acceptance over the years within the surgical community to the extent that current versions are referred to as the "Bovie". Such devices typically consist of a handle having a first or "active" electrode extending from one end. The other end of the handle is electrically coupled to an electrosurgical generator which provides a high frequency electric current in either an a.c. cutting mode or pulsed coaggulating mode. A remote control switch is attached to the generator and commonly is present as a foot switch located in proximity to the operating theater. During an operation, a second or "return" electrode, having a much larger surface area than the active electrode, will be positioned in contact with the skin of the patient. To remove tissue, the surgeon brings the active electrode into proximity with the tissue to be cut or coaggulated. This is a starting condition where the instrument has not touched tissue. At this point in time, the electrical switch is actuated whereupon the active electrode is brought into close proximity with the tissue to be cut. Electrical current then arcs from the active electrode and flows through tissue to the larger return electrode. In a cutting mode, the electrical arcing and corresponding current flow results in a highly intense but localized heating which causes cell destruction and tissue severance. Following a short cutting routine, the instrument again is elevated in still air away from the tissue for two or three seconds. In general, the device can be switched to a pulsed, higher voltage input to perform in a coaggulating mode.

Another common modality for electrosurgery is referred to as bipolar electrosurgery. With this approach, no large return electrode is in contact with the patient. Instead, each instrument is made having first and second electrodes arranged in close mutual proximity. The device is utilized with a dedicated bipolar cable which is inserted in appropriate bipolar outlets of an electrosurgical generator, a device found essentially in all major health care facilities. When switch activated, the bipolar device provides an electrical current which arcs from the end of a first electrode to the second. Tissue disposed between the electrodes is cut and blood may be coaggulated. In general, surgeons are trained in the use of both bipolar and monopolar modalities, however, particularly in conjunction with endoscopic applications, bipolar devices are becoming more accepted in view of safety considerations. In the latter regard, the bipolar approach overcomes certain of the more undesirable characteristics of monopolar instruments in that excessive necrosis is reduced and current is not passed extensively through the body of the patient. Since current arcs between adjacent electrodes, blood vessels readily are cauterized. Bipolar devices, however, generally exhibit a lesser quality cutting ability, and it is often difficult to accurately locate the arc between the two electrodes with respect to tissue under resection.

Typically, the ubiquitous electrosurgical generators exhibit outputs with frequencies ranging from about 350 KHz to 1 Mz. Such higher RF frequencies serve to avoid tissue stimulation which would otherwise occur at lower frequencies.

Investigators also have considered the implementation of resistive heating to carry out coagulation and cutting in surgery. Early devices employed a very fine wire formed as a loop or extending linearly between spaced mounting points. Formed, for example, of platimun, the thinness or small diameter of the heated wire was required in order to gain a high enough resistance to develop correspondingly high enough temperature levels in conjunction with practical current levels. The requisite thinness of the wire resulted in marginal strength or rigidity, thus restricting applications of such instruments to to spot coaggulation or very limited cutting procedures. Surgical blades have been developed with mechanically sharp edges and side mounted electrical heating elements. With these instruments, cutting is at the mechanically sharp facet of the blade, and the coaggulation or hemostasis is intended to develop as a result of contact of the sides of the blade with the cut tissue. This, unfortunately, represents and attempt to stop bleeding after cutting, as opposed to a more desirable procedure for simultaneous cutting with coaggulation. Of course, the possible damage resulting from use of a sharp instrument within the body cavity is inherent with these instruments. Another problem associated with these earlier thermally based surgical devices is that the wire or blade will rapidly cool upon contact with tissue. As the blade cools, it becomes less and less effective for providing hemostasis. Additionally, as the blade cools below a temperature threshold, tissue will tend to stick to it, resulting in an obstruction of the cutting edge. If additional power is supplied to accommodate for the cooling effect, overheating may occur in some regions of the blade. Such overheating may be accompanied by unwanted tissue burning or blade destruction.

More recently, resistively heated thermal devices have been introduced which may employ blunt cutting portions providing both cutting and coagulation. Such blunt cutting portions particularly are desirable for use with endoscopic applications. These devices utilize a thermal cutting portion emulating surgical blades and other implements which exhibits a self-regulating temperature characteristic. Self-regulation (also known as auto-regulation) involves maintaining the cutting surface of the surgical device within an elevated preselected temperature range. An approach for attaining self-regulation has been to employ a ferromagnetic material in constructing the end or heating element of the surgical instrument. When RF current is passed through such ferromagnetic material, current density tends to concentrate near its outer surface. This current density attenuates exponentially as distance into the material from the surface increases, a phenomenon known as the "skin effect".

The depth of the skin effect, i.e. the distance of penetrating current density into the ferromagnetic material, is defined as the depth at which current is reduced to approximately 37% of its surface value. This depth may be presented mathmatically as follows:

$$\text{skin depth} = C\sqrt{\frac{\rho}{\mu f}} \qquad (1)$$

where skin depth is measured in centimeters, $\rho$ is electrical resistivity in ohm-centimeters, $\mu$ is electrical relative magnetic permeability for the ferrogmagnetic material, C is a constant, e.g. $5 \times 10^3$, and f is frequency of the applied alternating electrical potential.

In ferrogmagnetic materials, such as iron, nickel, cobalt, and respective alloys, adjacent atoms and molecules couple their magnetic moments together in rigid parallelism (an interaction known as exchange coupling) in spite of the randomizing tendency of the thermal motion of atoms. If the temperature of such material is raised above a "Curie" temperature, specific for each ferromagnetic material, the noted exchange coupling suddenly disappears. As a result, these materials exhibit large changes in relative permeability as the temperature of the ferromagnetic material transitions through Curie temperature. As seen from equation (1), since the relative permeability is known to change in response to the temperature of the material, the associated skin depth also will change. This relationship between skin depth and temperature enables ferromagnetic material based instruments to achieve auto regulation.

The heating elements of surgical devices have been constructed from ferromagnetic material which is selected to have a Curie temperature at or near the auto-regulation temperature desired for a particular surgical application. As RF current passes through the ferromagnetic material, the heating element will resistively heat to approximately the Curie temperature. Once the cutting edge contacts tissue, both it and the area surrounding it will cool to a level below Curie temperature. In response to this Curie transition, skin depth will decrease which, in turn, results in an increased resistance of the cool region (the resistance being a function of the ferromagnetic material's resistivity multiplied by the length and divided by area). A corresponding increase in power supply will accompany this increase in resistance. The temperature then will tend to again increase due to resistive heating toward the Curie temperature. Thus, auto-regulation of the surgical component around the Curie temperature is achieved. See, for example, Eggers, U.S. Pat. No. 5,480,398, issued Jan. 2, 1996, entitled "Endoscopic Instrument with Disposable Auto-Regulating Heater"; and Eggers, et al., U.S. Pat. No. 5,480,397, issued Jan. 2, 1996, entitled "Surgical Instrument with Auto-Regulating Heater and Method of Using Same".

A disadvantage associated with resistively heated devices, including those which employ ferromagnetic heating elements, is concerned with a lack of sufficient localization of heat at the blunt cutting edge. In this regard, the entire heating element, including the support for its cutting edge, is heated toward a Curie temperature suited for cutting. This poses a risk that the support portion of the heating element may contact tissue or organs not selected for incision. Additionally, since a larger portion of the heating component is heated, the time period required for the cutting region to cool down to safe levels posing no threat of burn can be quite significant. This time period, for example, may be ten seconds or more, an interval, which in a surgical environment, is considered excessive, 2–4 seconds being considered acceptable, a starting condition interval to which surgeons are accustomed. Further, during laparoscopic or endoscopic procedures, the view of the surgeon is confined to a camera-generated two-dimensional image at a monitor, such as a TV screen. The heated element, however, may be moved out of the camera's limited field of view during the several seconds which are required for cool down, thereby posing a risk to tissue located adjacent the heated tip.

Another disadvantage associated with resistively heated devices has been concerned with the requirement that they must be powered by a specially designed or dedicated power supply. These dedicated electrical drive systems generally are configured to be unique to the properties of a particular heating element and are not of a universal nature, such that they would be usable with different surgical implements. In order to maximize the auto-regulation effect, the energy source used to apply power to the heating element preferably operates at a substantially constant current. Under constant current conditions, the amount of joulean power generated per unit length (i.e., current$^2$ × resistance) depends only on the effective resistance of the heating element, $R_{eff}$. The heating element resistance changes significantly as the temperature rises above the Curie temperature since the skin depth and associated current-conduction area, A, increases significantly above the Curie temperature. If a constant-voltage, alternating current power supply were used, the low heating element resistance which occurs when the heating element temperature exceeds the Curie temperature would result in a "thermal run-away" condition since joulean power dissipation, P, is inversely proportional to the resistance as shown below:

$$P = \frac{V^2}{R_{eff}} \qquad (2)$$

where P is joulean power dissipation, $R_{eff}$ is the effective resistance of the heating element, and V is constant voltage. For constant voltage V, as $R_{eff}$ decreases substantially above the Curie temperature, the power dissipation increases substantially resulting in excessively high heating element temperatures.

As a consequence of the foregoing considerations, practitioners have found it necessary to provide device dedicated electrosurgical generators for powering thermal implements. Of course, such added equipment requirements pose budgetary concerns to health care institutions.

SUMMARY

The present invention is addressed to surgical instruments of a variety having a resistively heated cutting component or element. In contrast to Curie temperature-based autoregulation devices, the instruments now presented perform sequentially in a starting condition and then an operating condition. In the starting condition, the heating element has not been brought into contact with tissue and, essentially, is in a still air environment. In a working condition, the heating component of the instrument is in contact with tissue for the purpose of carrying out cutting with coagulation. When in the starting condition, the instruments perform in reliance upon: (1) the fourth-power dependence of radiation heat transfer from the heating element; combined with (2) conductive thermal transfer along the thermally-conductive heating component support structure of the instrument, and (3) convective heat transfer. These three aspects of heat transfer function to regulate the temperature of the heating element within a range useful for applications of surgical cutting and coagulation of tissue. When in a working condition wherein the heating element is in contact with tissue, then heat transfer is by (1) conduction to tissue, and (2) thermal conduction through the thermally conductive supporting components of the instrument. When thus performing in conjunction with these two operational conditions, the heating elements are caused to remain within a predetermined temperature range having an upper temperature limit for the starting condition and a temperature threshold requirement for operation under the working condition. In effect, performance is achieved within the total temperature range of performance as a consequence of a correspondence between the total heat loss observed for the starting condition and the working condition.

To achieve this form of temperature-based performance, certain constraints are imposed upon the structure of the instrument. The temperature upper limit is required to be maintained at least at a value wherein the temperature of the heating component maintains the lower temperature threshold under a working condition which is effective to thermally cut and coagulate tissue. However, within the designated temperature range, the structural integrity of the heating component must be sustained and, for the interval of practical heating at the upper limit temperature, the surface of the heating element should not oxidize to the extent that "scale" or discrete oxide layers form thereon.

As another feature of the invention, the working assembly and instrument of the invention achieves a highly desirable rapid cool down upon the removal of electrical power at its heating element. Additionally, the instrument working end structure isolates the high temperature cutting region from the support components to the extent that the support components reside at temperatures atraumatic to tissue while the tissue engaging regions are at elevated tissue cutting temperatures. This advantageous operational feature is achieved through the selection of materials forming the heating element and support structure as well as through the configuration of those components. With such material selection and configuration, a thermal transition region is established within the heating component extending from its junction with the components supporting it.

A preferred material for the heating component is a ferromagnetic stainless steel. When this material is used, however, the upper limit temperature must be maintained below Curie temperature to achieve requisite stable resistivity by virtue of skin depth limited current flow.

This feature of excitation of the heating component or heating element by R-F current so as to remain below Curie temperature is in complement with the use of the surgical instrument with the bipolar output terminals of a conventional electrosurgical generator and its associated conventional bipolar cable. Through the use of impedance matching circuit components within the handle of the instrument, an expanded use of the bipolar modality is afforded the surgeon. In this regard, the surgeon may, for example, utilize bipolar scissors during one portion of a procedure and then, by simply plugging the bipolar cable to the present device, carry out cutting and/or coaggulation of tissue. This exchange among instruments may be carried out while the surgeon remains within the surgical field. As is apparent, through the use of the technique at hand, no dedicated, constant current electrosurgical generators are required, and the ubiquitous bipolar electrosurgical generator may be employed to minimize the cost of providing this new surgical tool.

An advantageous feature accrues from the resistivity defined current flow of the heating elements or components employed with the surgical instrumentation of the invention. In this regard, dissecting nodes or prods can be built within the heating component in a manner restricting current flow thereto such that the instrument may be employed as a prod as well as a thermal cutter and/or thermal coagulator.

Advantageously, the surgical instrument and system of the invention utilizes a working end assembly which is easily replaceable in the course of surgery within the surgical field. These working end assemblies may be fabricated at a cost commensurate with their use either as a disposble component, or one which may readily be sterilized for multiple uses. The replaceable tips also may include longer shafts for their adaptation to endoscopic or laparoscopic procedures.

The invention, accordingly, comprises the apparatus and system possessing the construction, combination of elements, and arrangement of parts which are exemplified in the following detailed disclosure. For a fuller understanding of the nature and objects of the invention, reference should be made to the following detailed description taken in connection with the accompanying drawings.

BRIEF DESCRIPTION OF THE DRAWINGS

FIG. 6 is an exploded view of an instrument according to the invention showing additionally an endoscopic embodiment thereof;

FIG. 7 is a sectional view taken through the plane 7—7 shown in FIG. 6;

FIG. 8 is a sectional view taken through the plane 8—8 shown in FIG. 7;

FIG. 9 is a sectional view taken through the plane 9—9 shown in FIG. 6;

FIG. 10 is a sectional view taken through the plane 10—10 seen in FIG. 9;

DETAILED DESCRIPTION

The thermally cutting and coaggulating surgical instruments described herein, when implemented with cutting components formed of preferred ferromagnetic material, are not autoregulated about Curie temperature. Their design is predicated upon a performance at temperatures which continuously remain below Curie temperature. Thus, the cutting components continuously exhibit high resistance for optimum heat generation while retaining a desired structural integrity. Performance of the cutting components within stable temperature ranges is achieved through the utilization of the radiation heat transfer, convective heat transfer, and instrument-based conductive heat transfer during starting conditions characterized as being in still air prior to any physical contact with tissue. This stable starting condition temperature then permits generation of a stable thermal cut temperature above a thermal cut threshold value within a working condition environment in contact with tissue. During this working condition environment, heat transfer from the cutting component is a function substantially only of thermal conduction into the tissue and into the surgical instrument.

The present surgical instrument functions in complement with existing bipolar surgical systems. The handle component of its support structure incorporates circuit components carrying out power transfer impedance matching between the bipolar output terminals of a conventional electrosurgical generator and the heating component. As a consequence, the bipolar cable otherwise utilized with the bipolar terminals of the electrosurgical generator may be employed with the instant instrumentation. Accordingly, the surgeon may employ conventional bipolar components such as bipolar scissors which are coupled to this cable and then, while still within the surgical field, remove the scissors from the cable and insert the instrument of the invention, and continue with the surgery. No dedicated constant current electrosurgical power sources are required with the present system. Thus, the system of the invention supports an observed trend in the surgical arena tending to favor the utilization of bipolar electrosurgical systems.

Figure 1:
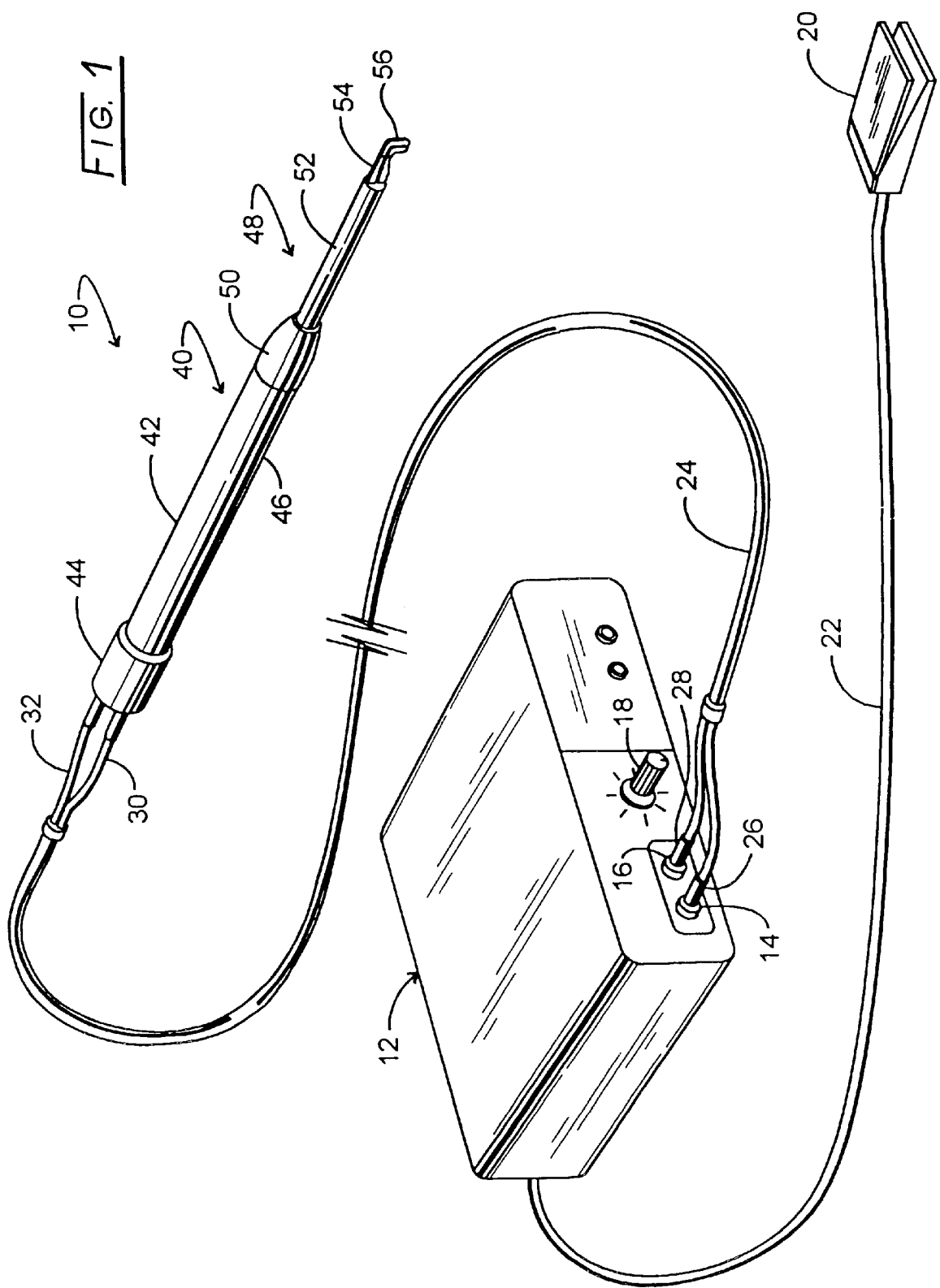
FIG. 1 is a perspective view of a surgical instrument according to the invention coupled via a bipolar cable to the bipolar terminals of an electrosurgical generator.

Referring to FIG. 1, a system for carrying out the thermal hemostatic cutting of tissue is represented in general at 10. System 10 employs a conventional electrosurgical generator shown generally at 12 and which incorporates two bipolar output terminals 14 and 16 as well as hand manipulated controls such as represented by the knob 18. Various levels of bipolar output power from the generator 12 may be selected by the adjustment of knob 18. The bipolar output at terminals 14 and 16 is activated, for example, by the actuation of a foot pedal 20 seen coupled to it via a cable 22. Generators as at 12 are marketed, for example, by Conmed/Aspen of Utica, N.Y.; Berchtold of Tuttlingen, Germany; Birtcher of Irvine, Calif.; Erbe of Tübingen, Germany; Martin of Tuttlingen, Germany; and Valleylab of Boulder, Colo. A conventional bipolar cable 24 is provided in conjunction with the generator 12. Cable 24 has two connector components 26 and 28 which plug into respective terminals 14 and 16. At the opposite end of this elongate cable 24, corresponding connector components 30 and 32 are seen plugged into a surgical instrument according to the invention as represented generally at 40. Instrument 40 is configured for carrying out conventional open surgical procedures and includes a handle or hand engageable instrument handling portion 42 having a rearwardly disposed male connector housing 44 with terminals for removable connection with cable 24 connector components 30 and 32. The hand graspable intermediate portion 46 of handle 42 serves to support circuit components which are selected for carrying out a power transfer impedance matching between the bipolar output terminals 14 and 16, and the cutting component of instrument 40. Attached to the forward end of handle 46 is a working end assembly represented generally at 48 which may be of a disposable variety. Assembly 48 includes a rearward support portion 50 having two male terminals which plug into the forward end of handle portion 46 for purposes of transmitting current. Support portion 50, in turn, supports an intermediate support portion 52 formed principally of thermally and electrically conductive components. The front end of intermediate support portion 52 is coupled in electrical and thermal conductive relationship with a forward support portion or assembly 54 formed of electrically and thermally conductive material which, in turn, is coupled for electrical and thermal conduction with an angularly oriented heating element or component 56. It may be observed from the figure that intermediate thermally and electrically conductive region 52 is of substantially greater cross section than the forward support components at 54. However, the configuration of that region 52 is of a diametric extent or cross section not hindering the vision of the surgeon in observing the action of the heating component 56.

Figure 2:
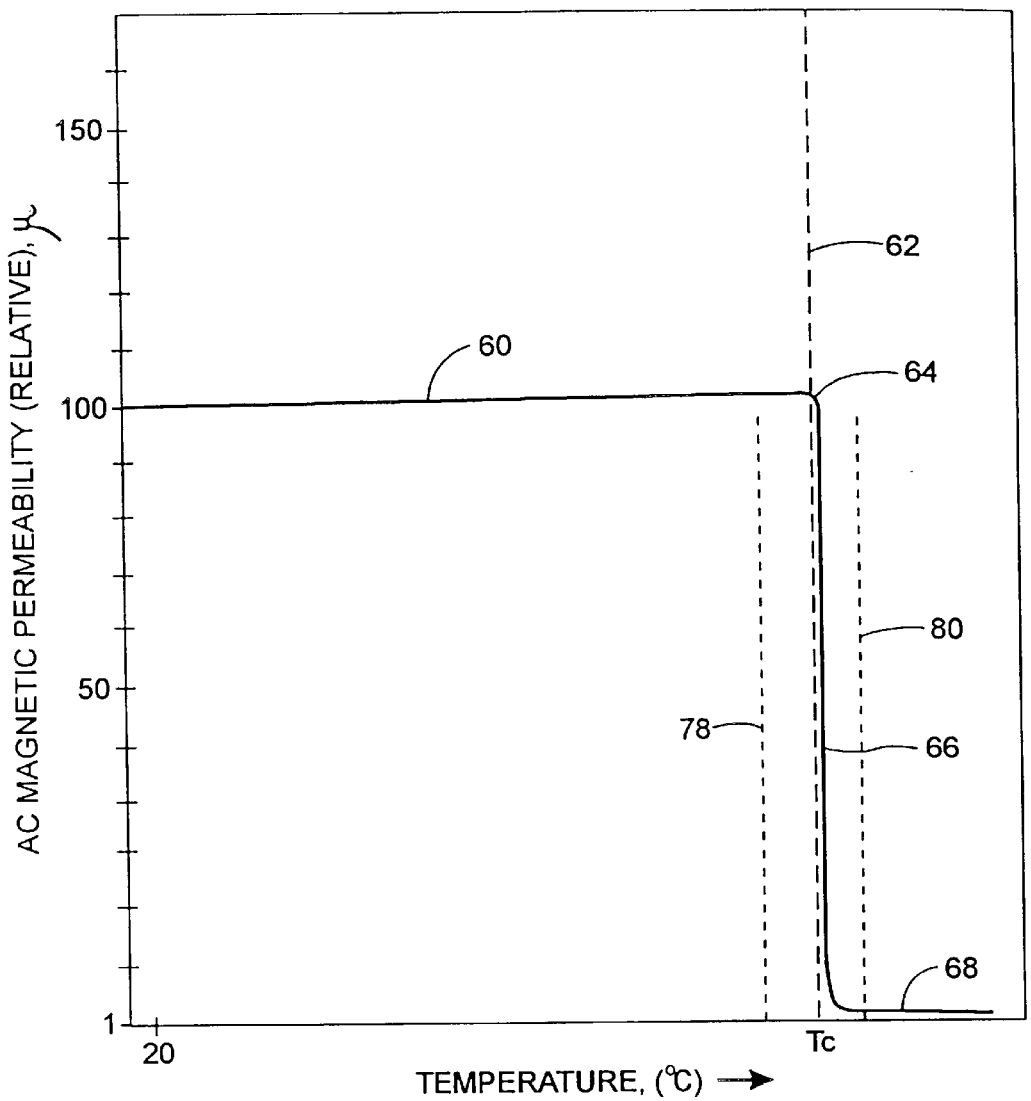
FIG. 2 is a graph relating a A.C. magnetic relative permeability with temperature and illustrating the operation of surgical instruments in autoregulation about Curie temperature.

Referring to FIG. 2, a plot of A.C. relative magnetic permeability with respect to temperature in degrees centigrade for a given heating element is represented at curve 60. In the figure, the Curie temperature, $T_c$, for the material at hand is represented by that designation in conjunction with a dashed vertical line 62. Note that line 62 intersects the knee of curve 60 at 64, whereupon the relative magnetic permeability evidenced by the curve rapidly drops, as represented at region 66, to a relative magnetic permeability approaching unity value as represented at region 68. For the example shown, the relative magnetic permeability abruptly changes from a value of about 100 at or just above Curie temperature, $T_c$, to a value of unity at region 68. For a given heating element, the unaffected resistance exhibited thereby, $R_o$, may be valued as follows:

$$R_o = \frac{\rho L}{A} \tag{3}$$

Where $\rho$ is electrical resistivity in ohm-centimeters, L is the length of the heating element in centimeters, and A is the cross-sectional area of the heating element in centimeters squared.

Figure 3:
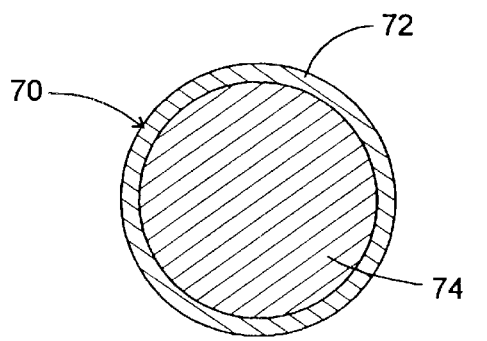
FIG. 3 is a cross-section of a ferromagnetic material illustrating skin effect.
Figure 4:
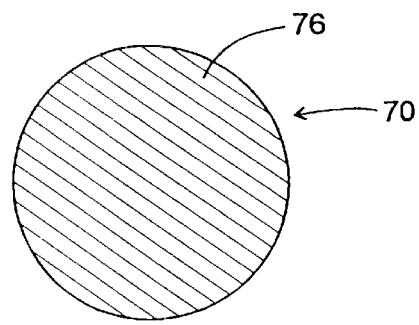
FIG. 4 is a cross-section of ferromagnetic material illustrating operation above Curie temperature.

Referring to FIG. 3, a cross-sectional view of a circular heating element 70 is revealed. Where the element 70 is formed of a ferromagnetic material exhibiting a relative magnetic permeability of about 100 as represented at curve 60, and is at temperatures below Curie temperature, $T_c$, then current flow will be restricted to an outer (skin) region represented by the cross-hatched annulus 72. Substantially no current will be flowing within the interior region 74 of element 70. Under such conditions, the effective resistance of element 70, $R_{eff}$ will be about 10 times greater than the unaffected resistance, $R_o$. However, referring to FIG. 4, where the temperature of heating element 70 is elevated above Curie temperature, $T_c$, then the relative magnetic permeability drops toward unity as represented at region 68, and substantially the entire cross-section of element 70 as represented at cross-hatched area 76, functions to conduct current. Under this condition, for example where autoregulated devices are held away from tissue and in still air, then the effective resistance, $R_{eff}$, is equal to the unaffected resistance, $R_o$. The region of performance for autoregulated devices may then be represented as that extant within temperatures extending between the dashed lines 78 and 80 in FIG. 2. In this regard, dashed line 80 represents the maximum operating temperature of a heating element under autoregulation, while dashed line 78 represents the minimum operating temperature for an autoregulated element. Generally, the temperature excursion represented by the distance between lines 78 and 80 will correspond to about 50 to 75° C.

In contrast to Curie temperature-based autoregulating devices, the surgical instruments and systems as now presented recognize and thus utilize the fourth power dependence of radiation heat transfer from a heating component, as well as convection heat transfer and thermally conductive heat transfer effected by the thermally conductive support components 52 and 54 to develop the temperature of the heating element or component 56 at levels within a range useful for surgical cutting and coaggulation of tissue. Heating components 56 are configured to exhibit a resistance wherein temperatures may be derived within a range having an upper limit which is determined by the maximum allowable rate of oxidation of the material of the device in air and further in consideration of requisite mechanical strength of the heating component at these elevated temperatures. At the maximum operational temperature values, the heating element or component should not oxidize to the extent that "scale" or discrete oxide layers form on its surface. Such layers would impede the transfer of heat to tissue being cut and/or coagulated. Further, in this regard, the upper temperature limit with respect to oxidation is one associated with the time of energization at those temperature levels. In general, the time interval at such higher temperatures is that under a start condition of relatively short interval and under somewhat intermittent conditions representing a relatively short duty cycle. Furthermore, the heating element or component should maintain its mechanical integrity at the maximum operating temperatures such that forces applied to it during cutting and coagulating tissue will not result in its significant deformation. This upper limit is a function of the heating element material selected and, possibly, the properties of any optional thin oxidation resistant coating. The optional use of such an oxidation resistant coating must be accomplished so that the electrical resistance of the heating component or element, when energized by high frequency current, is not significantly reduced. Where the preferred feromagnetic materials are employed, the temperatures for performance must always lie below Curie temperature, $T_c$, in order to take continuous advantage of the skin effect phenomenon.

The lower temperature limit or limit temperature of the heating component or element is the subject of several considerations. This lower limit temperature is one which is developed as a thermal cut threshold value within a working condition environment. That working condition environment is one wherein the heating component is in contact with tissue. Under this working condition, heat transfer from the heating component is a function substantially only of thermal conduction into the tissue and into the supporting assemblies 52 and 54 of the instrument 40. To be effective for the surgical purpose at hand, the heated element or component must be capable of transferring sufficient heat to the tissue to seal severed blood vessels as they are cut or contacted. Next, the temperature of the heating component must remain sufficiently high to prevent adherence of tissue and coagulant to it. Such materials, when sticking to the heating element, may impede heat transfer to tissue and/or cause the evulsion of the sealing layer formed to cover any severed blood vessels. In general, tissue does not stick to the heating component at temperatures of about 400–500° C. At such temperatures, any material which would otherwise tend to cling to the heating component carbonizes. A third optional requirement is that, in surgical procedures where it is preferred that the probe not have a mechanically sharp cutting edge such as in endoscopic procedures, the temperature of the heating component must remain high enough to effect thermal cutting of tissue. This latter thermal cutting requirement and the requirement to avoid sticking of tissue limit the useful operating range of the heating component to temperatures of about 400–450° C. This minimum temperature or lower limit temperature, in turn, places a constraint on the minimum upper limit operating temperature of the heating component. Specifically, the upper limit operating temperature of the heating component (i.e., when that component is energized while in still air in a starting condition), must be sufficiently high such that the combined above-described radiation, convection, and conduction through instrument heat losses are comparable and correspond to the maximum heat dissipation while under a working condition in contact with tissue and carrying out cutting and/or coagulating. The upper limit typically will be about 650–700° C., and the lower limit temperature of the heating component should be held to the noted 400–450° C. to carry out effective cutting and coagulation.

Figure 5:
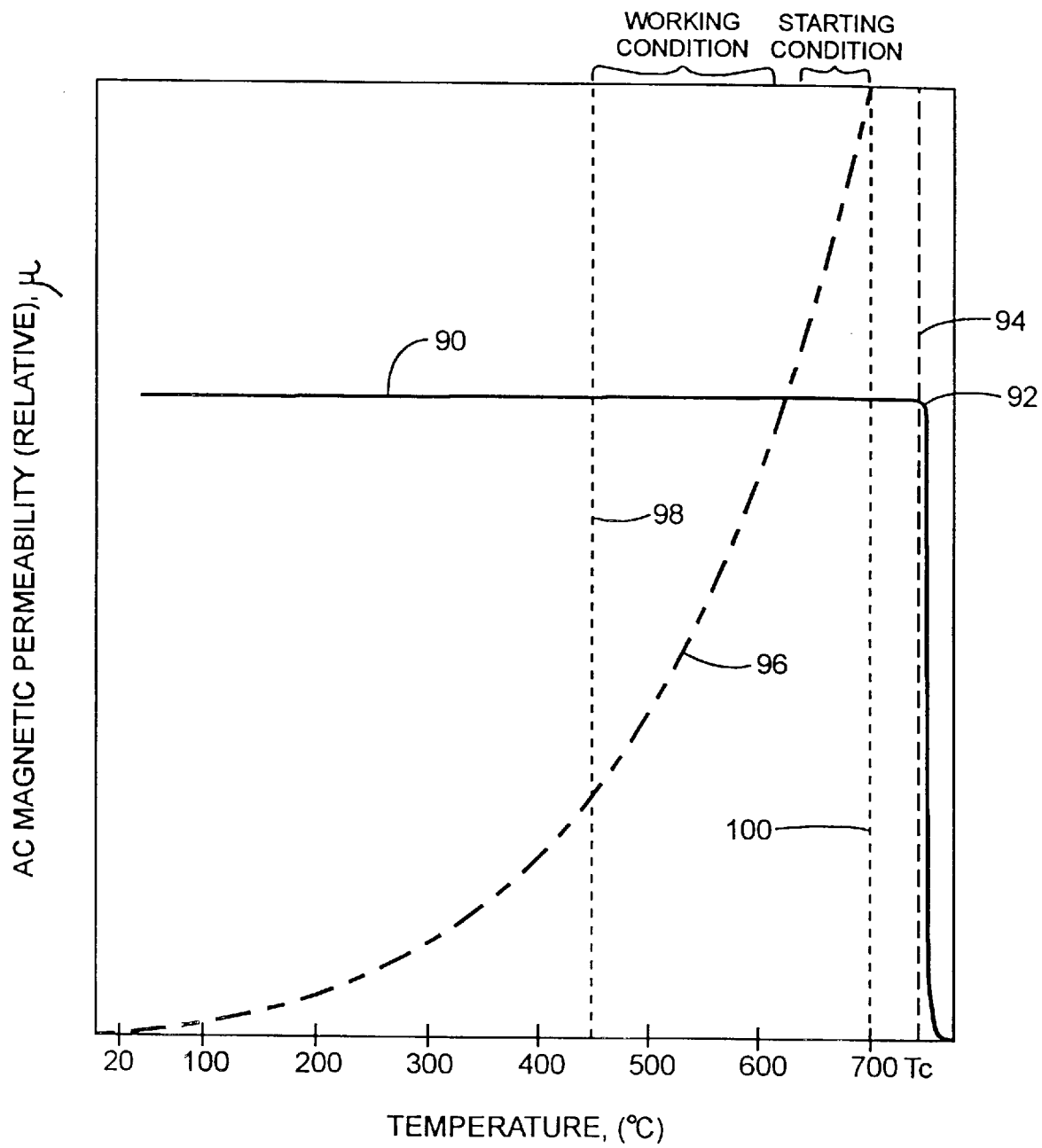
FIG. 5 is a graph relating A.C. magnetic relative permeability with temperature and illustrating the operation of the instant system below Curie temperature.

Referring to FIG. 5, these starting condition and working condition criteria are illustrated graphically. The figure is similar to FIG. 2 and is provided in conjunction with a ferromagnetic material embodiment showing a curve representing A.C. relative magnetic permeability as at 90, the knee of which at 92 establishes a Curie temperature, $T_c$, as represented at dashed line 94. A curve 96 illustrates heat loss from the heating element as at 56 as a function of temperature. Curve 96 has an exponential form in consequence of the effective heat loss due to radiation in still air with respect to temperature. This radiation heat loss is a fourth power function. However, the curve 96 also reflects loss in still air due to convection and conductive heat dissipation through the instrument and, specifically, through forward support portion 54 and intermediate support portion 52. Performance of a heating element along curve 96 is shown to be between the lower limit or threshold temperature of 450° C. and an upper limit temperature of 700° C. as represented, respectively, by dashed lines 98 and 100. Performance under a still air starting condition where the heating element is not in contact with tissue is shown by the labeled bracket on the figure, while the temperature range for the working condition of the heating element in contact with tissue is labeled with an adjacent bracket commencing at a 450° C. lower limit temperature.

Now considering the materials employed in forming the heating component as at 56, those electrically resistive materials may encompass both ferromagnetic and non-ferrogmagnetic materials. If a preferred ferromagnetic material is selected, then its Curie temperature must be higher than the upper operating temperature limit of the material in order to maintain a skin effect defined electrical resistance. Other constraints on the selection of the heating components or heating element material include the following:

1. Surface oxidation rate at the maximum operating temperature should be sufficiently low to minimize discrete scale formation.

2. The mechanical strength of the material should be sufficiently high over the operating temperature range to prevent deformation or breakage during procedures for cutting and coagulation of tissue.

3. For systems wherein existing electrosurgical generators with bipolar output ports or terminals are used, the electrical resistance of the heating element should be compatible either (a) directly with the output impedance characteristics of the electrosurgical generator, or (b) with impedance matching circuitry placed between the electrosurgical generator and the heating element, i.e. within the handle portion as at 42 of instrument 40.

4. The material or any coating thereon must be biologically compatible with human tissue.

5. The material must exhibit characteristics for deriving a thermal transition region therewithin in conjunction with the support structure with which it is bonded in electrical and thermal conduction. In general, this calls for material exhibiting low thermal conductivity, K, and high electrical resistivity, ρ.

A material meeting all of the above requirement is a cutlery-grade stainless steel. For example, martensitic stainless steel alloy 420 meets these requirements, exhibiting a Curie temperature of 730° C. which is above the nominal upper operating temperature limit of about 650° C. The material, being ferromagnetic, provides the advantage that current flows only on the skin of a heating element or component formed of it throughout the entire range of operating temperatures as illustrated and described in connection with FIG. 5. Additionally, these operating temperatures are achieved while the cross-sectional area of any heating element or component formed of the material may be sufficiently large to meet the mechanical requirements for tissue manipulation, cutting and coagulation, as well as the thermal requirements for efficiently conducting joulean beat generated around the entire perimeter of the heating element to that portion of the heating element in contact with tissue. Use of this particular ferromagnetic alloy simplifies impedance matching with existing electrosurgical generators. Should the heating element resistance be too low, then impedance matching becomes difficult or impossible to incorporate into a practical hand-held device. A compilation of other possible ferromagnetic materials whose Curie temperature is acceptably high for surgical applications is presented in Table 1 below. The suitability of any such materials depends upon their meeting the above-listed requirements, with or without an appropriate oxidation-resistant biocompatible coating.

TABLE 1

Composition (Percent) (Balance of Composition is iron)

| Ferromagnetic Alloy | C | Cr | Ni | Mn | Mo | Co | Si | Other | Cure Temp. (C.) |
|---|---|---|---|---|---|---|---|---|---|
| Stainless Steel 403-Ara | 0.15 | 12.50 | | 1.00 | | | 0.50 | | 730 |
| Stainless Steel 405 (Ferritic)-Ara | 0.08 | 11–14 | | 1.00 | | | 1.00 | 0.1–0.3% Al | 720 |
| Stainless Steel 414 (Bozroth p722) | 0.15 | 12.50 | 2.00 | 1.00 | | | 1.00 | | 720 |
| Stainless Steel 420 (Boxroth p722) | 0.15 | 13.00 | | 1.00 | | | 1.00 | | 730 |
| Iron/Silicon Alloy (Bozroth p79) | | | | | | | 4.00 | | 750 |
| Iron/Cobalt Alloy (Heck p142) | | | | | | 49 | | 2% V | 980 |
| Vicalloy (Heck p703) | | | | | | 52 | | 9–11% V | 850 |
| Mild Steel (Bozroth p870) | 0.2 | | | | | | | | 770 |
| Permandur (Bozroth p870) | | | | | | 50 | | | 980 |
| Cobalt (Bozroth p870) | | | | | | 99 | | | 1120 |
| Vanadium Permandur (Bozroth p870) | | | | | | 49 | | 1.8% V | 980 |
| Hiperco (Bozroth p870) | | 0.5 | | | | 35 | | | 970 |
| TAF-Hitachi Metal Co. (Ara) | Proprietary | | | | | | | | 730 |

The above information set forth in Table 1 is derived from the following references:

Heck, C., "Magnetic Materials and Their Applications"., Crane, Russack & Company., Inc., New York, N.Y. (1974).

Bozroth, R. M., "Ferromagnetism", D. Van Strand Company, Princeton, N.J. (1951).

Ara, K., "Magnetic Characteristics of Ferromagnetic Stainless Steels", IEEE Transactions on Magnetics, Vol. 25, No. 3, pp 2617–2623 (1989)

The resistance exhibited by a heating element or component configured as described at 56 and coupled with a forward support component as shown at 54 was experimentally evaluated with respect to operating temperatures at room temperature and at 700° C. The heating component or element was formed of martensitic stainless steel Alloy 420 as coupled by welding with supporting components formed of copper. The Bozroth reference of Table 1 indicates that the Curie temperature for this heating element material is 730° C. Previous experimental observations, including the use of thermocouples and calibrated colorimetry, have shown that the heating element under investigation reaches a temperature of about 650–700° C. when energized under still air conditions, i.e. starting conditions wherein it is not in contact with tissue. When the heating element is brought into contact with tissue under working conditions, that portion of the heating element in contact with the tissue decreases to about 450° C. For the instant investigation, a chromel/alumel thermocouple was spot welded to the heating element as described at 56. The inputs to the heating element or component as extending through supports 54 were coupled to a frequency source provided as a Leader LFG-13005 function generator, and the thermocouple was coupled to a fluke thermocouple measuring instrument. The frequency source was set to provide a sinusoidal output. A 50 ohm non-inductive resistor was incorporated within the frequency source input leads and a Hewlett-Packard 3400A true RMS voltmeter was coupled through a 1:1 ratio isolation transformer to a shunt positioned across the 50 ohm resistor and to the noted outputs of the heating component and the associated forward support. Next, the voltage measurement leads from the 50 ohm load resistor were circuit completed to the RMS voltmeter. Then, the output of the signal generator was increased until the measured voltage, V, reached 0.50 volts RMS. This value corresponds to a current, $I_p$ of 10 milliamps, inasmuch as I=V/R and R has a 50 ohm value. Then, the voltage taps leading to the voltmeter were changed to read across the heating element so as to measure the voltage $V_p$. The heating element resistance, R, then was calculated using Ohms Law wherein R equals $V_p/I_p$. Then, a flame from a propane torch was applied to the heating element until its temperature, as measured by the thermocouple and associated measurement device, reached 700° C. The color of the heating element as at 56 at this point in time was observed to be a bright yellow/orange.

The above procedure commencing with the connecting of voltage measurement leads from the RMS voltmeter to the orientation across the 50 ohm load resistor were repeated while maintaining the heating element or component at the temperature of 700° C. The above steps were carried out for a frequency from the frequency source of 500 KHz and at 1000 kHz.

The results of the above experimental procedure are summarized in Table 2 below. This table shows that the resistance increases on the order of about 10% and, although the heating element or component is a ferromagnetic material, it does not undergo a significant change of resistance over the operating temperature range investigated, i.e. below the published Curie temperature.

cable 24 are easily coupled electrically with the handle portion 42 at the male connector housing 44. Further, the working end assembly 48 is readily coupled to the handle 42, all of these procedures being easily carried out by the surgeon within a surgical field.

Working end assembly 48 also may be configured for endoscopic or laparoscopic utility. In this regard, an endoscopic working end assemlby is represented generally at 110. Assembly 110 is configured essentially identically as that at 48, with the exception of its length. In this regard, the assembly includes a rearward support portion 112 identical to that shown at 50. Component 112 includes a necked down portion of cylindrical configuration 114 which functions to suppport two male mini-banana connectors 116 and 117 which correspond to connectors 104 and 105. The intermediate support portion 118 of assembly 110 is substantially identical to that at 52 with the exception of its extended length. Intermediate support portion 118, in turn, is thermally and electricaly coupled in supporting relationship with forward support portion 120. Forward support portion 120 is thermally and electrically coupled to heating component 122.

Referring to FIG. 7, the internal components of handle 42 are revealed. In the figure, the male connector assembly 44 is seen to be formed having two cylindrical chambers formed therein as at 122 and 124. Mounted within these chambers are respective banana type male connectors 126 and 128. The assembly 44 is configured having a necked down cylindrical portion 130 which slides within the internal cavity 132 of hand graspable intermediate portion 46, the face 134 of portion 130 abutting against an annular seat 136 formed within cavity 132. Connectors 126 and 128 extend through the portion 130 and are coupled to the primary side of a transformer represented generally at 138. This primary side of transformer 138 is comprised of insulatively coated

TABLE 2

| Probe Number | Probe Temp. | Measured Voltage Across 50 ohm Resistor (volts RMS) | Calculated Current ($I_p$) (milliamps) | Measured Voltage ($V_p$) Across Probe Input (volts RMS) | Calculated Resistance $V_p/I_p$ (ohms) | Frequency |
|---|---|---|---|---|---|---|
| 12-27-1 | 22° C. | 0.50 | 10.0 | 0.0111 | 11.2Ω | 1.0 MHz |
|  | ~700° C.* | 0.50 | 10.0 | 0.0115 | 1.15Ω | 1.0 MHz |
|  | 22° C. | 0.50 | 10.0 | 0.0111 | 1.11Ω | 1.0 MHz |
|  | ~700° C.* | 0.50 | 10.0 | 0.0116 | 1.16Ω | 1.0 MHz |
| 12-27-1 | 22° C. | 0.50 | 10.0 | 0.0050 | 0.50Ω | 500 kHz |
|  | ~700° C.* | 0.50 | 10.0 | 0.0054 | 0.54Ω | 500 kHz |
|  | 22° C. | 0.50 | 10.0 | 0.0050 | 0.50Ω | 500 kHz |
|  | ~700° C.* | 0.50 | 10.0 | 0.00545 | 0.545Ω | 500 kHz |

*Probes heated to upper limit of operating regimen using propane flame to elevated probe temperatures.

Now looking to the structure of the instrument 40, reference is made to FIG. 6 wherein the device is shown in disassembled or exploded fashion. Connector components 30 and 32 of bipolar cable 24 terminate in female connectors which are inserted within cylindrical openings formed in male connector assembly 44 within which are mounted banana type connectors. Handle portion 42 is formed as a cylinder having an internal cavity, the forward region of which establishes a receiver region 102. Region 102, in turn, carries an insert with female connectors suited to receive the mini-banana connectors 104 and 105 extending rearwardly outwardly from a necked down cylindrical extension 106 of rearward support 50 of the working end assembly 48. With the arrangement, the connector components 30 and 32 of wire wound about the secondary side and core structure of transformer 138 and having each end coupled to connectors 126 and 128 as shown, respectively at 140 and 142. The core of transformer 138 is fashioned of four open cylindrical or pipe-like structures sometimes referred to as "doughnuts" which are coaxially aligned and represented at 144–147. The material utilized for core components 144–147 is selected to provide efficient coupling between the electromagnetic fields of the primary and secondary windings at the operating frequency of electrosurgical generator 12, which for typical commercially available generators, ranges from about 350 KHz to 1 MHz. A preferred core material is magnesium-zinc-ferrite which is manufactured by the Magnetics Division of Sprang & Co., Butler, Pa.

The secondary side of transformer 138 is formed as an outer copper clad 150 and a centrally disposed pipe-like or cylindrical copper component 152. A secondary output is provided by a lead 154 soldered to cylindrical inner copper component 152 and coupled, in turn, to one side of a capacitor 156 and an insulated lead 158 which is soldered to copper clad 150. The power supplied by generator 12 to heating component 56 may be adjusted through the use of various circuit tuning techniques. By way of example, a capacitance value capacitor 156 is selected based upon the reactance of transformer 138 which, in turn, is dependent upon the frequency of generator 12. Accordingly, a specific capacitance for capacitor 156 is selected to optimize power delivery corresponding to the output frequency of generator 12. For example, the capacitance value of capacitor 156 may be selected for use with generators operating in the 400 KHz range. Such value would be decreased for use with generators operating in the 500–600 KHz range. For those generators operating at even higher frequencies, the capacitance value for capacitor 156 may be further decreased. In each case, the value selected should be based upon maximum power delivery to heating component 56 under cutting and coagulating conditions. This circuitry also is a feature of the invention permitting the adaptation of the instrument 40 to use with the ubiquitous pre-existing electrosurgical generators generally available in health care facilities. Both those generators, functioning through their bipolar terminals as well as the cables associated therewith as at 24 are afforded additional utilization through the placement of the circuitry for impedance matching within the handle 42. In this regard, were impedance matching located at the generator housings themselves, then the cable 24 would be required to be structured so as to accommodate high currents. Next, because of this impedance matching at the handle 42, the surgeon may switch from conventional bipolar instruments to the present instruments while still remaining within the surgical field. Thus, the surgeon is given greater latitude and convenience with the entire bipolar instrument modality.

Lead 158 from the transformer as well as lead 160 from capacitor 156 are coupled to respective female terminals 162 and 164 which are mounted within a polymeric forward insert 166 seated upon a shoulder 168 formed by the cavity 102. To access to the terminals 162 and 164 for purposes of inserting a working end assembly as at 48 with greater ease, insert 166 is chamfered at the terminal openings as at 170 and 172. Looking additionally to FIG. 8, it may be observed that the insert 166 is retained in position within handle 42 by a set screw 174 threaded to the outer shell 176 of the handle, and into a cavity 178 formed within forward insert 166.

Referring to FIG. 9, intermediate support portion 52, forward support portion 54, and heating component 56 are illustrated at an enhanced level of detail. The design of these facets of the invention is one taken in contemplation of the need for heat dissipation under starting conditions in still air, as well as the localization of cutting coagulating level heat at heating component 56. It is also quite important to isolate the high temperature, tissue engaging portion of component 56, as well as to effect a rapid cool down of the heating component 56 upon removal of power. This interval for cool down should be commensurate with that of conventional electrosurgical devices, i.e. in the 2–5 second interval range. The localization of heat and associated rapid cool down serve to avoid unwanted damage to adjacent tissue and organs.

The highly advantageous feature of isolating the high temperature development at heating component 56 while additionally attaining a rapid cool down phenomena is achieved through a design which combines the structure and materials of heating component 56 and forward support portion 54 in a manner in which a thermal transition region is developed extending inwardly within the heating component from the union of these structures. In general, heating component 56 is designed to exhibit low thermal conductivity, K, and low thermal conductance, C. In general, the latter parameter may be expressed by the equation:

$$C = \frac{L}{KA} \qquad (4)$$

where A is the cross-sectional area of the heating component. In addition to low conductance (high thermal resistance, R), the structure of heating component 56 must exhibit high electrical resistivity, $\epsilon$, as well as high electrical resistance, R. Electrical resistance in the general or nominal sense may be represented as follows:

$$R = \frac{\rho L}{A} \qquad (5)$$

where L is the length of the component under consideration, and A is its cross-sectional area. The second aspect of developing a thermal transition region or thermal choke resides in the design of forward support portion 54. This forward support portion should exhibit low electrical resistivity, $\rho$, and low electrical resistance, R. The latter parameter may be expressed as shown above in connection with equation (5). Next, the support component 54 should exhibit high thermal conductivity, K, and high thermal conductance, the latter parameter being discussed above in connection with equation (4). The association of these "high"–"low" design features serves to evoke the noted thermal transition region.

Figure 11:
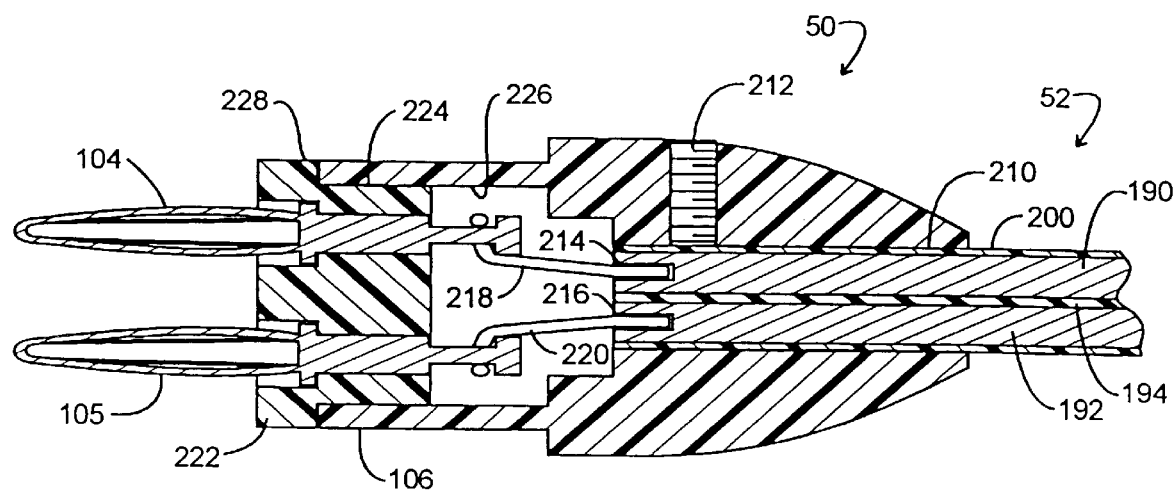
FIG. 11 is a sectional view taken through the plane 11—11 shown in FIG. 6.

Returning to FIG. 9, it may be observed that forward support portion or assembly 54 is configured having two spaced apart legs 182 and 184 formed of material exhibiting the requisite high thermal conductivity and low electrical resistivity. Examples of such material include copper, silver, aluminum, molybdenum, or alloys based on one or more of those metals. The configuration of the material used in support portion 54 should be selected to minimize joulean heating as RF current passes therethrough and to maximize heat conduction from heating component 56. In this regard, heating component 56, being formed, for example, of ferromagnetic material such as 420 stainless steel is welded to legs 182 and 184 at the weld seams respectively shown at 186 and 188. Legs 182 and 184 also must provide structural support to the heating component 56. Generally, where legs 182 and 184 are formed, for example, of copper, their thickness will be about 32–35 mils in extent. Typically, where the heating component 56 is formed of 420 stainless steel, its thickness will be about 25–27 mils, and one may observe about a 5–7 mil step at the seams 186 and 188. RF current to carry out joulean heating at heating component 56 is passed through legs 182 and 184 from respective rods 190 and 192. Looking additionally to FIG. 10, rods 190 and 192 are seen to be fashioned to resemble elongate half cylinders in terms of cross-section. They are spaced apart by an electrically insulative layer 194. Electrically insulative layer 194 may be provided as a polyimide film which exhibits physical, electrical, and mechanically stable properties over a wide temperature range. Such materials are marketed under the trade designation KAPTON® by E.I. DuPont de Nemours Company. The insulative material also is marketed as a film tape with a silicon pressure sensitive adhesive by Minnesota Mining and Manufacturing Company, Industrial Tape and Specialties Division, St. Paul, Minn. as a "Scotch" brand electrical grade tape number 92. Each of the legs 182 and 184 is formed having a rearwardly extended tab portion shown, respectively, at 196 and 198, which fits within a corresponding slot formed within respective rods 190 and 192. These tabs 196 and 198 are soldered in such position to provide electrical and thermal conduction between components 54 and 52. The entire assemblage is retained together by a polymeric shrink wrap 200, a portion of which at 202 extends beyond the forward surfaces of rods 190 and 192 to provide a sealing cavity which is filled with an insulative epoxy (not shown). With the arrangement shown, heat dissipation via the phenomenon of thermal conduction is provided from heating component 56 through the legs 182 and 184 and thence along rods 190 and 192 toward the handle 42. Note in this regard that the cross-section of the rods 190 and 192 is substantially greater than that at legs 182 and 184. This improves conductive heat dissipation and the rods will have, for example, a maximum width of 0.187 inch in the absence of the shrink wrap 200. This provides for an overall diameter for open surgical application which does not hinder the vision of the surgeon. The length of rods 190 and 192 for that open surgical application will be about 1⅜ inch. As such, and looking to FIG. 11, the rods 190 and 192 along with electrically insulative layer 194 and the wrap 200 extend to the rearward support portion 50. Portion 50 is formed of polymeric material with a centrally disposed cylindrical opening formed therein as seen at 210. The rod assembly is retained in position by a set screw 212. Each of the rods 190 and 192 is rearwardly inwardly bored, respectively as at 214 and 216, so as to receive electrical leads shown, respectively, at 218 and 220. Leads 218 and 220 are shown foreshortened in the interest of clarity and are connected to the inwardly disposed portions of mini-banana connectors 104 and 105. Connectors 104 and 105 are seen to be connected to a cylindrical rear insert 222, having a necked down portion 224 which is slideably retained in adjacency with the internal surface 226 of necked down portion 106. The insert 222 is seated against portion 106 at an annular shoulder 228. With the arrangement shown, the working end 48 readily is assembled upon the handle 102 and may be replaced with ease by the practitioner.

Figure 12:
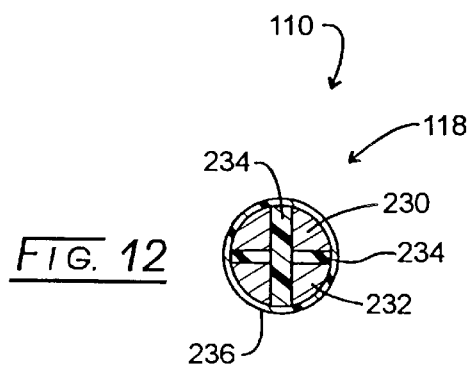
FIG. 12 is a sectional view taken through the plane 12—12 shown in FIG. 6.

Returning to FIG. 6 and looking to FIG. 12, for the elongate endoscopic version 110 of the instrument, the copper cylindrical rods may be retained in alignment through the utilization of a sequence of polymeric pins. In this regard, FIG. 12 shows copper rods 230 and 232 being retained in alignment by one such pin as shown at 234. In the same figure, the electrically insulative layer earlier described at 194 is shown at 234 and a shrink wrap covering is shown at 236. For a typical embodiment of the endoscopic version of the instrument, five such plastic pins are employed having center-to-center spacing varying from 1 inch to 3 inches. The diametric extent of intermediate support portion 118 may be equivalent to that at 52, a dimension promoting insertion through typical cannulas employed with endoscopic-laparoscopic surgery.

Figure 13:
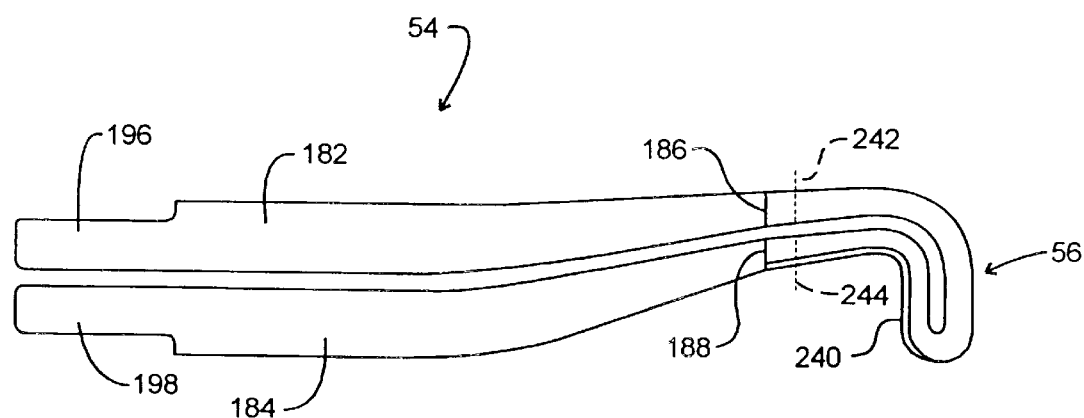
FIG. 13 is a plan view of a forward support assembly and heating component shown in FIG. 6.

Referring to FIG. 13, forward support portion or assembly 54 and heating component 56 are shown in enlarged fashion. The electrical resistance heating component 56 extends between two termini located at seams 186 and 188. In typical utilization of the configuration shown, a V-shape is formed at 240 and the component 56 typically is drawn toward the surgeon when making a cutting with hemostasis maneuver.

Recalling the above discourse concerning the importance of isolating the portions of heating component 56 which engage tissue from the supporting components of the instrument, by selecting the geometry and materials forming the heating component 56 and the supporting legs 182 and 184, a thermal transition region can be created which extends outwardly from the seams 186 and 188 to dashed boundaries, for example shown, respectively at 242 and 244. The extent of the thermal transition regions depends upon selection of materials and geometry including cross-sectional area. The region of heating component 56 extending outwardly from the boundaries 242 and 244 may be deemed a tissue engaging portion which will exhibit those high temperatures requisite for thermal cutting and coagulation. However, the gradient from boundary 242 and 244 to respective seams 186 and 188 is such as to bring the temperature at those seams substantially to levels atraumatic to tissue. Thus, as noted above, to evoke the transition regions extending from seams 186 and 188, the heating component 56 is formed to exhibit low thermal conductance and high electrical resistance. Geometry including length and cross-sectional area are part of the evolution of these parameters as well as the selection of materials exhibiting low thermal conductivity and high electrical resistivity. The thermal transition regions extending, for example, to the boundaries 242 and 244 from respective seams 186 and 188 will exhibit a thermal resistance greater than about 200° C./watt. In contrast, the legs 182 and 184 of the forward support assembly 54 will exhibit low electrical resistance to avoid Joulean heating as well as high thermal conductance. For example, the inverse parameter of thermal resistance will be of a value for these legs 182 and 184 of less than about 100° C./watt. With the arrangement, the temperature levels during cutting and coagulation of regions 182 and 184 will be below 60°–70° C. The heat further is conducted from the legs 182 and 184 to the rods 190 and 192 or their equivalents in the case of the endoscopic embodiment of the invention.

Figure 14:
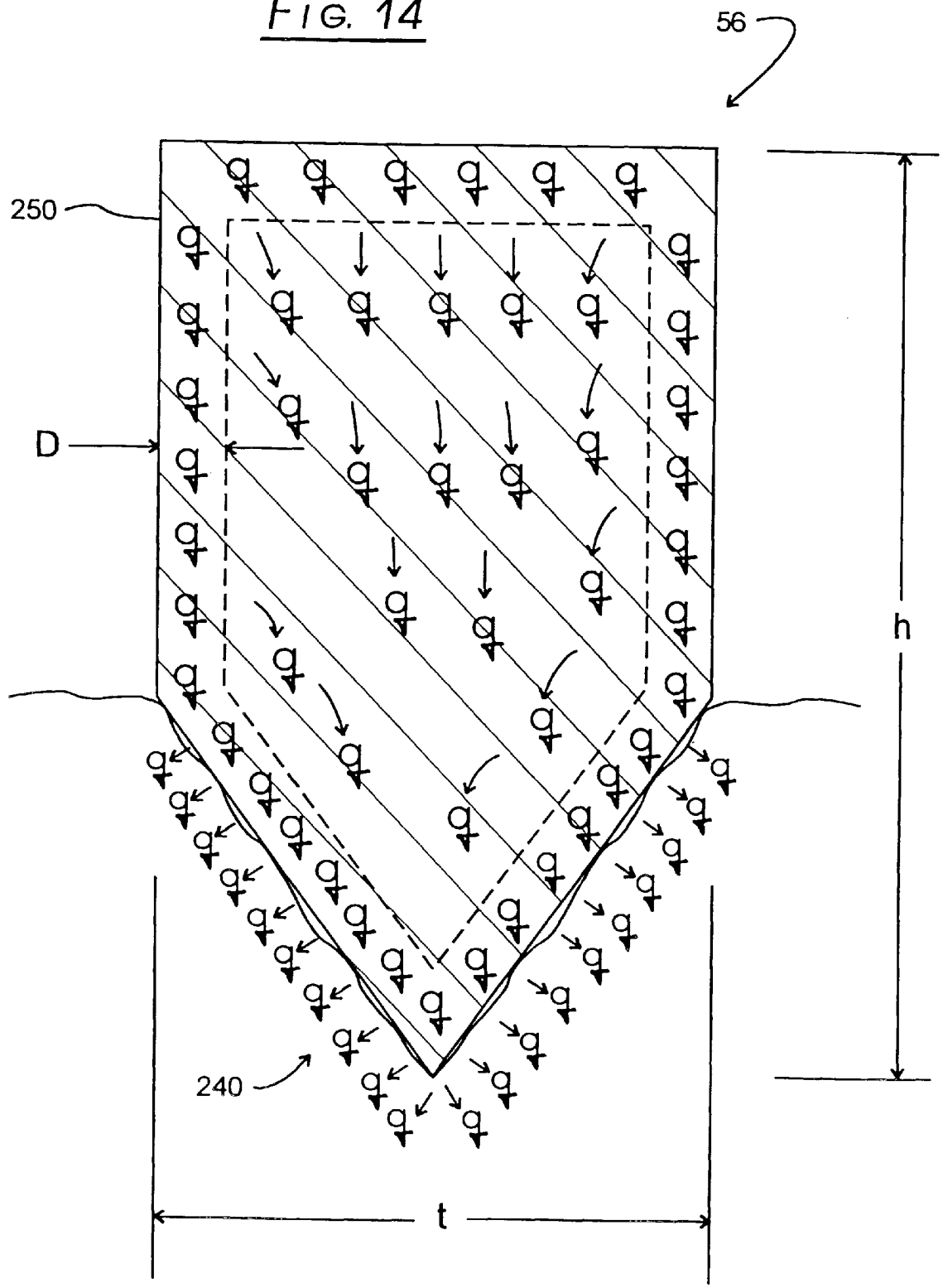
FIG. 14 is a schematic representation of the section of a heating component according to the invention illustrating thermal migration.

Referring to FIG. 14, a schematic representation of the V-shaped contact region 240 of heating component 56 is revealed. It is assumed for the present illustration that the material from which heating component 56 is formed is ferromagnetic, for example stainless steel 420. Under the noted operational criteria, as discussed in connection with FIG. 5, the temperature of component 56 always is below Curie temperature, $T_c$, and at a value above a lower limit or threshold temperature effective to thermally cut tissue, for example about 400–450° C. The upper limit temperature, which occurs when in a starting condition permits the instrument to achieve that lower limit temperature for cutting with hemostasis when contact with tissue is made. The current conducting region of component 56 for this below Curie temperature condition is represented at shaded border region 250 representing the skin effect or effective depth of current flow. For the instant demonstration, the thickness of the heating component 56 will be from about 0.5–0.7 mm as is represented at "t" in the figure, and the height of the component, h, will range from about 0.7–1.4 mm. In general, the effective depth of current flow will range from about 0.01 mm to 0.03 mm depending upon the operating frequency of the generator 12 and the properties of the ferromagnetic material at hand. In the figure, generated heat is represented by groupings of q characters. The conductive migration of this heat is represented by the arrows associated with that symbol, substantial thermal conduction being evoked from the skin region 250 through the entire component cross-section toward the V-shaped region 240 where conductive heat transfer is carried out between the component 56 and adjacent tissue. The result of this heat migration provides that most of the total joulean heat flows into the tissue contacted by the heating component 56. Only a small amount is lost to air from portions of the component 56 not in contact with tissue.

Figure 15:
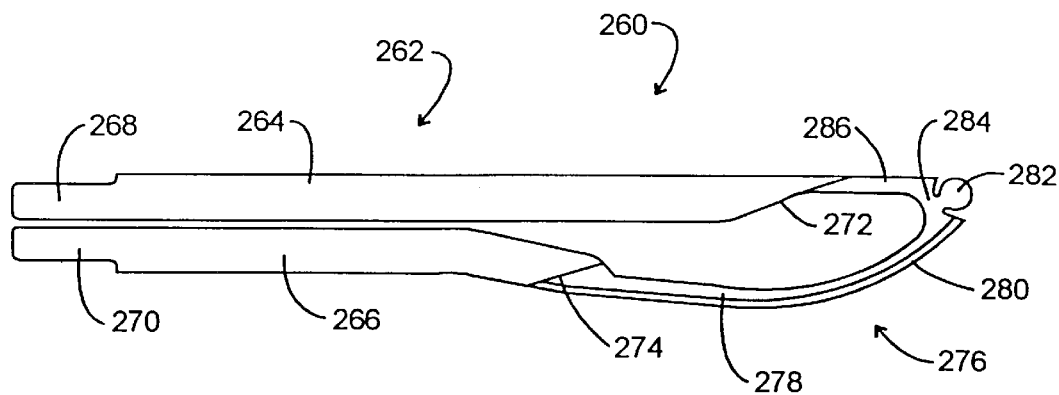
FIG. 15 is a plan view of a forward support and heating component assembly according to the invention showing a probe portion.

Referring to FIG. 15, another configuration for the combination of forward support portion and heating component of the instrument 40 is revealed in general at 260. In this embodiment, the forward support assembly 262, as before, is configured having two thermally and electrically conductive legs which are spaced apart and are configured with respective tab portions at 268 and 270. The forward ends of legs 264 and 266 are shown respectively at 272 and 274 defining a seam at which the termini of a heating component shown generally at 276 are weldably attached. Heating component 276 has a tissue engaging portion generally shown at 278 shaped to emulate the shape of a conventional scalpel with a V-shaped edge 280. A rounded prod portion 282 is integrally formed within the component 276 and is seen to extend from a neck region 284. With the arrangement shown, current will tend to pass at skin depth along the tissue engaging portion 278 and the upper disposed portion 286 but will refrain from passing into the prod portion 282 because of the greater resistance to current flow in the neck region 284. Thus, the prod 282 will not reach the temperature of the remainder of heating component 276, thermally induced heat tending to migrate to the tissue engaging portion 278 as described in conjunction with FIG. 14 above. The configuration combining thermally conductive forward support 262 with the heating component 276 at the seams 272 and 274 also provides for development of the earlier-discussed thermal transition regions within the heating component 276 extending inwardly from the seams 272 and 274.

Figure 16:
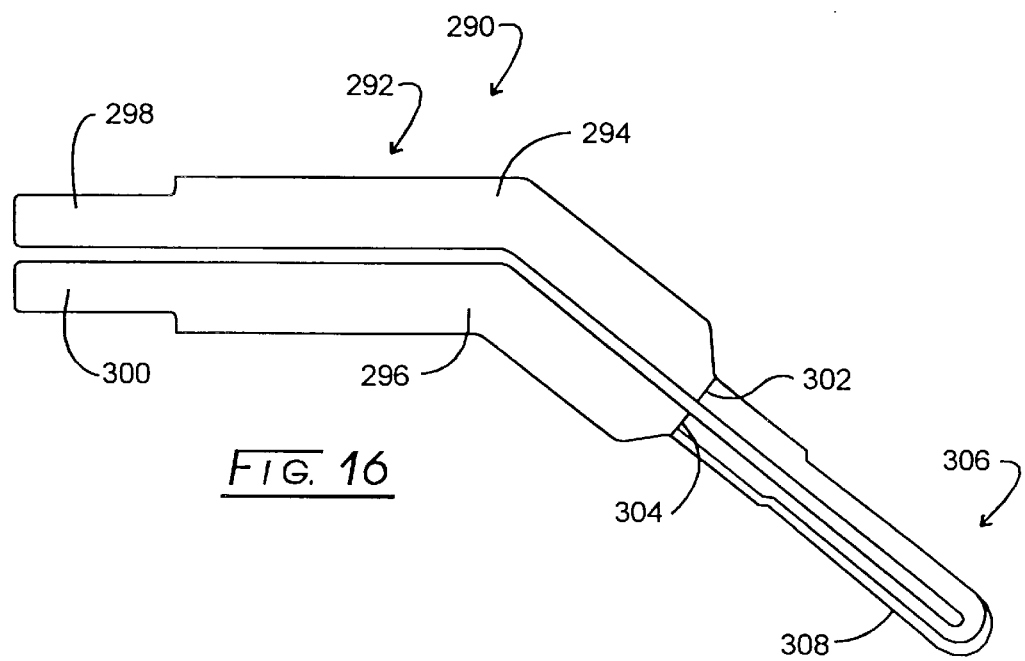
FIG. 16 is another configuration for a forward support assembly and heating component configured according to the invention.

Looking to FIG. 16, a combined forward support assembly and heating component sub-assembly is represented at 290 having a configuration of a canted dissector. The forward support assembly is shown at 292 having two spaced apart legs 294 and 296. The rearward portions of legs 294 and 296 are formed having respective tab portions 298 and 300 for attachment with the intermediate support assembly described in conjunction with FIGS. 9 and 10. The forward ends of legs 294 and 296 are at respective seams 302 and 304 at which position a dissector shaped heating component 306 is attached. As before, the heating component 306 preferably is formed of a ferromagnetic stainless steel such as stainless steel 420, while the forward support assembly 292 is formed of an electrically and thermally conductive material exhibiting a thermal resistance value of less than about 100° C./watt. Heating component 306 is weldably attached to the ends of legs 294 and 296 at its termini and includes a V-shaped tissue engaging portion in the region represented generally at 308

Figure 17:
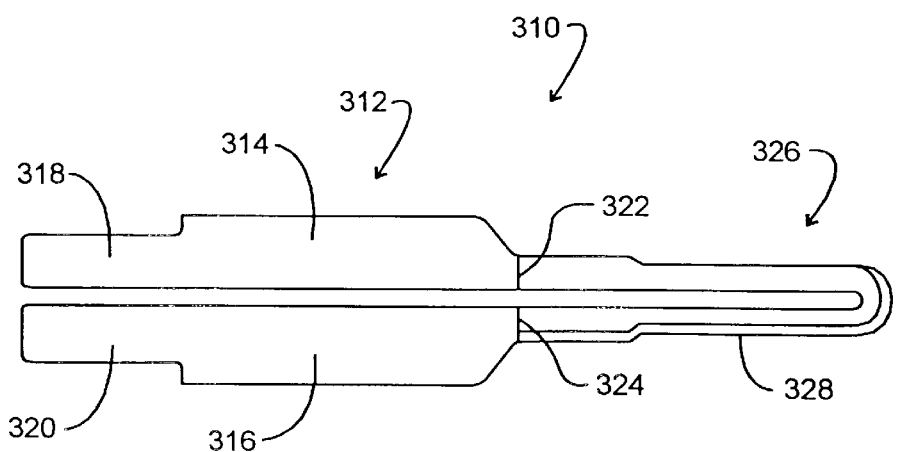
FIG. 17 is a plan view of a forward support assembly and heating component combination configured according to the invention.

Referring additionally to FIG. 17, a straight dissector configuration of a heating component and forward support assembly is represented in general at 310. Configuration 310 includes a forward support assembly shown generally at 312 which is configured having spaced-apart legs 314 and 316 with rearwardly disposed tab portions 318 and 320. These tab portions, as before, are configured for attachment with rods as described at 190 and 192 in connection with FIGS. 9 and 10. The forward ends of legs 314 and 316 are present at welding seams shown, respectively, at 322 and 324, which function to couple the heating component 326 to legs 314 and 316. Heating component 326, as before, preferably is formed of ferromagnetic material to take advantage of the skin effect. Component 326 is configured having a tissue engaging portion in the region represented generally at 328.

It may be observed in FIGS. 16 and 17 that the thermal transition regions established within heating components 306 and 326, as they extend outwardly from the joining seams shown, respectively, at 302, 304, and 322, 324, are configured having cross sections of greater extent than the tissue engaging regions represented, respectively, at 308 and 328. Note in this regard that the thermal transition regions at 340 and 342 within component 306 have a greater widthwise dimension than the tissue engaging region 308. Similarly, the thermal transition regions 344 and 346 of heating component 326 have greater cross-sectional extents than the tissue engaging region 328. In this regard, the greater cross-section is developed through enlarging the widthwise extent at these regions. This arrangement achieves an enlargement of the value, A, representing cross-sectional area, which functions to achieve a low thermal conductance, C, as described in conjunction with equation (4) above. By utilizing this geometric contribution to the definition of the thermal transition regions, the high temperature tissue engaging regions are more readily identified by the surgeon, a helpful visual cue. As before, in keeping with the above criteria, the preferred material for the forward support assemblies 290 and 312 is a thermally and electrically conductive material exhibiting thermal resistance values of less than about 100° C./watt. Further, the thermal transition regions should exhibit low thermal conductance and high telectrical resistance, for example a thermal resistance greater than about 200° C./watt.

Since certain changes may be made in the above-described appparatus and system without departing from the scope of the invention herein involved, it is intended that all matter contained in the description thereof or shown in the accompanying drawings shall be interpreted as illustrative and not in a limiting sense.

I claim:

1. A working end assembly for connection with a surgical instrument and responsive to electrical power supplied from a source for carrying out thermal cutting of tissue with hemostasis, comprising:

a heating component extending continuously from a first terminus to a second terminus, having a tissue engaging region located between said first and second termini, said heating component being formed of material exhibiting low thermal conductivity and high electrical resistivity and configured to exhibit low thermal conductance and high electrical resistance for deriving a substantially, repeatably stable start temperature, at a predetermined level above a lower limit temperature effective to thermally cut tissue, within a starting condition air environment with thermal regulation which derives said predetermined level only by heat transfer therefrom as a function substantially only of radiation, convection, and conduction to said surgical instrument in response to the application of a value of said power from said source, and for deriving a substantially stable thermal cut temperature above said lower limit temperature within a working condition environment in contact with said tissue in response to application of said value of power from said source, with heat transfer therefrom as a function substantially only of thermal conduction into said tissue and to said surgical instrument; and a support portion formed of electrically and thermally conductive material configured having first and second ends in current and heat transfer communication with respective said first and second termini and having a second portion in heat dissipating relationship with said first support portion.

2. The working end assembly of claim 1 wherein said heating component is configured for deriving a said start temperature predetermined level of at least about 450° C.

3. The working end assembly of claim 2 in which:

said heating component is formed of ferromagnetic material exhibiting a predetermined Curie temperature, Tc; and said start temperature predetermined level is less than said Curie temperature, Tc.

4. The working end assembly of claim 3 in which said Curie temperature, Tc, has a value greater than 700° C.

5. The working end assembly of claim 1 in which said support assembly first support portion extends in thermal exchange relationship with said second portion, said second portion being rearwardly disposed, thermally and electrically conductive and connectable in supported relationship with said instrument.

6. The working end assembly of claim 5 in which said first support portion is formed of a material exhibiting low electrical resistivity and high thermal conductivity for evoking with said heating component first and second thermal transition regions extending toward said tissue engaging region from respective said first and second termini and exhibiting a temperature at said first and second termini atraumatic to tissue.

7. A working end assembly for connection with a surgical instrument handle and responsive to electrical power supplied from a source for carrying out thermal cutting of tissue with hemostasis, comprising:

an electrical resistance heating component extending from a first terminus to a second terminus, having a tissue engaging region located between said first and second termini, said heating component being formed of material exhibiting low thermal conductivity and high electrical resistivity and configured to exhibit low thermal conductance and high electrical resistance, and responsive to an applied current to generate heat at said tissue engaging region at temperature levels effective for carrying out said thermal cutting of tissue with hemostasis;

a forward support portion having first and second electrically and thermally conductive spaced apart legs of first cross-sectional extent formed of material exhibiting low electrical resistivity and high thermal conductivity and configured to exhibit low electrical resistance and high thermal conductance effective for evoking with said heating component first and second thermal transition regions extending toward said tissue engaging region from respective said first and second termini and exhibiting a temperature at said first and second termini atraumatic to tissue, said first and second spaced apart legs extending to respective first and second rearward ends;

an intermediate support portion having first and second rods of second cross sectional extent greater than said first cross sectional extent, each formed of a thermally conductive material exhibiting a thermal resistance value of less than about 100° C./watt, mutually electrically insulatively spaced apart, having respective first and second front ends coupled in heat transfer communication with respective said first and second forward support portion rearward ends and having respective first and second rear ends; and a rearward support portion coupled in supporting relationship with said intermediate support portion adjacent said first and second rear ends, connectable with said surgical instrument handle and said source for effecting the conveyance of current to said heating component.

8. The working end assembly of claim 7 in which said first and second rods are formed of electrically conductive material and are configured to convey current from said source from said rearward support portion respectively to said first and second legs of said forward support portion.

9. The working end assembly of claim 8 in which:

said first and second rods are configured generally as elongate half cylinders having respective first and second elongate flat surfaces positioned in mutually facing relationship; and including an electrically insulating layer located intermediate said first and second flat surfaces.

10. The working end assembly of claim 9 in which said rearward support portion is configured as a polymeric plug having first and second electrical connectors removably connectable with said surgical instrument handle and electrically coupled with respective said first and second rods.

11. A system for carrying out the thermal hemostatic cutting of tissue, comprising:

an electrosurgical generator having bipolar output terminals exhibiting a load impedance to voltage characteristic;

a surgical instrument including:

an electrical resistance heating component extending from a first terminus to a second terminus, having a tissue engaging region located between said first and second termini, said heating component being formed of material exhibiting low thermal conductivity and high electrical resistivity and configured to exhibit low thermal conductance and high electrical resistance for deriving a substantially repeatably stable start temperature at a predetermined level above about 450° C. within a starting condition air environment with heat transfer therefrom as a function substantially only of radiation, convection, and conduction to said surgical instrument in response to the application of an applied current, and for deriving a substantially stable thermal cut temperature above a thermal cut threshold value within a working condition environment in contact with said tissue in response to application of said current, with heat transfer therefrom as a function substantially only of thermal conduction into said tissue and to said surgical instrument, a forward support portion having first and second electrically and thermally conductive discrete legs of predetermined first cross-sectional extent formed of a thermally conductive material exhibiting a thermal resistance value of less than about 100° C./watt, configured having first and second forward ends in heat transfer communication with respective said first and second termini and extending to respective first and second rearward ends, an intermediate support portion having first and second rods of second cross sectional extent greater than said first cross sectional extent, each formed of a thermally conductive material exhibiting a thermal resistance value of less than about 100° C./watt, mutually electrically insulatively spaced apart, having respective first and second front ends coupled in heat transfer communication with respective said first and second forward support portion rearward ends and having respective first and second rear ends, a rearward support portion coupled in supporting relationship with said intermediate portion adjacent said first and second rear ends, and having an electrical input for conveying current to said heating component, and a hand engageable instrument handling portion having circuit components selected for effecting power transfer impedance matching between said bipolar output terminals and said heating component, having an instrument output coupled with said electrical input and having an instrument input; and an elongate cable connectable in electrical power transfer relationship between said bipolar output terminals of said electrosurgical generator and said instrument input of said instrument handling portion.

12. The system of claim 11 in which:

said heating element is formed of ferromagnetic material exhibiting a predetermined Curie temperature, Tc; and said start temperature predetermined level is less than said Curie temperature, Tc.

13. The system of claim 12 in which said Curie temperature, Tc, has a value greater than 700° C.

14. The system of claim 11 in which said forward support portion first and second legs are formed of a material exhibiting low electrical resistivity and high thermal conductivity for evoking with said heating component first and second thermal transition regions extending toward said tissue engaging region from respective said first and second termini and exhibiting a temperature at said first and second termini atraumatic to tissue.

15. The system of claim 11 in which said first and second rods are formed of electrically conductive material and are configured to convey current from said source from said rearward support portion respectively to said first and second legs of said forward support portion.

16. The system of claim 15 in which:

said first and second rods are configured generally as elongate half cylinders having respective first and second elongate flat surfaces positioned in mutually facing relationship; and including an electrically insulating layer located intermediate said first and second flat surfaces.

17. A working end assembly for connection with a surgical instrument and responsive to electrical power supplied from a source for carrying out thermal cutting of tissue with hemostasis, comprising:

an electrical resistance heating component extending from a first terminus to a second terminus, having a tissue engaging region located between said first and second termini and having a cutting portion configuration exhibiting a first resistance to current applied from said source for deriving a temperature of value effective for carrying out said thermal cutting of tissue with hemostasis and having a prod portion configuration extending from a neck region of predetermined second resistance defining extent limiting the passage of said current to said prod portion to a value developing a temperature value at said prod portion atraumatic to tissue; and a support assembly formed of thermally and electrically conductive material exhibiting a thermal resistance value of less than about 100° C./watt, configured having first and second ends in heat transfer communication with respective said first and second termini and extending to an oppositely disposed connector portion for connection with said surgical instrument; and said support assembly and said tissue engaging portion deriving first and second thermal transition regions extending inwardly from respective said first and second termini effective to restrict the temperature level exhibited at said support assembly to values atraumatic to said tissue when said support assembly is in contact therewith.

18. A working end assembly for connection with a surgical instrument and responsive to electrical power supplied from a source for carrying out thermal cutting of tissue with hemostasis, comprising:

an electrical resistance heating component extending between first and second termini, having a tissue engaging region located between said first and second termini exhibiting a first cross-sectional area for carrying out said thermal cutting and at temperatures above about 300° C., said heating component being formed of material exhibiting low thermal conductivity and high electrical resistance, having first and second thermal transition regions respectively extending from said first and second termini toward said tissue engaging region and having a second cross-sectional area greater than said first cross-sectional area and exhibiting a thermal resistance greater than about 200° C./watt; and a forward support assembly having first and second legs with respective first and second ends in electrical and heat transfer communication with said first and second termini, each said first and second legs being formed of thermally conductive material and exhibiting a thermal resistance value of less than about 100° C./watt for evoking said first and second thermal transition regions.

* * * * *